United States Patent
Horiuchi et al.

[11] Patent Number: 5,286,194
[45] Date of Patent: Feb. 15, 1994

[54] DENTAL HANDPIECE HAVING TURBINE ROTATABLE IN REVERSE DIRECTION

[75] Inventors: Hiroshi Horiuchi, Sendai; Sosaku Kawata, Kanuma, both of Japan

[73] Assignee: Nakanishi Dental Manufacturing Co., Ltd., Kanuma, Japan

[21] Appl. No.: 974,861

[22] Filed: Nov. 10, 1992

[30] Foreign Application Priority Data

Nov. 12, 1991 [JP] Japan .................... 3-295930

[51] Int. Cl.⁵ .................................. A61C 1/05
[52] U.S. Cl. .......................... 433/132; 415/904
[58] Field of Search .............. 433/132, 82; 415/904

[56] References Cited

U.S. PATENT DOCUMENTS

| | | | |
|---|---|---|---|
| 3,082,528 | 3/1963 | Reid | 433/132 |
| 3,175,293 | 3/1965 | Borden | 433/132 |
| 3,270,417 | 9/1966 | Stram | 415/906 |
| 3,439,422 | 4/1969 | Doeden et al. | 415/904 |
| 3,609,058 | 9/1971 | Tarsoly | 433/132 |
| 3,942,392 | 3/1976 | Page, Jr. et al. | 415/904 |
| 4,146,964 | 4/1979 | Lares et al. | 415/904 |
| 4,303,393 | 12/1981 | Gentry | 433/132 |
| 4,326,846 | 4/1982 | Sugai et al. | 433/132 |
| 4,341,520 | 7/1982 | Wallace | 433/132 |
| 4,786,251 | 11/1988 | Ruegsegger | 433/132 |

Primary Examiner—Paul J. Hirsch
Attorney, Agent, or Firm—Joseph C. Mason, Jr.; Ronald E. Smith; Makoto Kanesaka

[57] ABSTRACT

A dental handpiece having a turbine rotatable in reverse contains a main handpiece body, a turbine head mounted at a distal end of the main handpiece body, a plurality of turbine vanes for rotatably driving a dental tool romovably mounted within the turbine head, a first air supply passage for ejecting compressed air to one surface of each of the turbine vanes for rotating the turbine vanes in one direction, a second air supply passage for ejecting compressed air to the other surface of each of the turbine vanes for rotating the turbine vanes in the other direction, and an air discharge passage for discharging the compressed air.

7 Claims, 4 Drawing Sheets

DENTAL HANDPIECE HAVING TURBINE ROTATABLE IN REVERSE DIRECTION

BACKGROUND OF THE INVENTION

This invention relates to a dental handpiece having a turbine rotatable in reverse direction, whereby a dental tool attached to the handpiece may be driven in forward and reverse directions for dental treatment.

A dental handpiece having attached thereto a dental tool for grinding a tooth or a metal prosthetic material has been used extensively. A driving device such as an impeller driven under an air pressure, a water conduit and air supply/discharge conduits are provided within the inside of the dental handpiece. The dental tool having a grinding tip end is adapted for being rotated by the driving device. In dental treatment, dental tools having a grinding ends suited to the positions or shapes of the sites of treatment or to the objectives of treatment are selected and selectively attached to a tool head such as turbine head.

FIG. 7 is a front view showing a conventional dental handpiece. An air supply conduit 2 and an air discharge conduit 3 are separately formed within a handle part 1 of the handpiece, as shown in FIG. 8, and compressed air is supplied from an air tube 4 into the air supply conduit 2. The air supply conduit 2 and the air discharge conduit 3 are separated from each other by a partition 5 within the handle part 1. A turbine blade 7 is rotatably mounted within a turbine head 6. A central shaft 8 of the turbine blade 7 is rotatably supported by bearings, not shown. A dental tool 9 is attached to the central shaft 8 by, e.g. a chucking unit, not shown, for grinding the tooth or the metal prosthetic material.

With the above-described dental handpiece, compressed air is supplied from the air tube 4 via the air supply conduit 2 to the turbine head 6 so as to impinge via the end of the conduit 2 onto the turbine blade 7 for rotating the turbine blade 7 about the central shaft 8 as the center of rotation. By the rotation of the turbine blade 7, the air is discharged from the space between vanes 7a via the discharge conduit 3. The turbine blade 7 is rotated at an elevated speed by the compressed air to cause rotation of the dental tool 9 in a predetermined direction for grinding the tool.

Meanwhile, as shown in FIG. 9, when the marginal edge of a metal prosthetic material 11 such as an inlay filled in tooth is cut by the above-described dental handpiece, it is preferred that rotation of the dental tool 9 be in a direction of from the metal prosthetic material 11 towards the tooth surface, so that a part of the metal prosthetic material 11 is not extended from the tooth surface, that is, in order to prevent irregularities from being produced on the edges of the metal prosthetic material 11 or to prevent a gap from being produced between the metal prosthetic material 11 and the tooth.

Besides, for adapting the metal prosthetic material 11 to the defect portion of the tooth 12 after removal of the site of lesion in the course of treatment of tooth caries, and for retaining the metal prosthetic material 11 against the biting force, it is necessary to cut a basically rectangular tooth cavity 13 to attach the prosthetic material 11 in the so-formed cavity 13, as shown in FIG. 10. At this time, the fundamental procedure is to rotate the dental tool 9 in a direction proceeding from the tooth towards outside, that is in a direction of flying the debris towards outside, because otherwise a smooth marginal edge cannot be obtained.

However, with the conventional dental handpiece, the direction of flow of compressed air through the air supply conduit 2 and the air discharge conduit 3 is constant, so that the dental tool 9 can be rotated only in one direction. Consequently, for cutting left and right teeth or cutting left and right sides of the same tooth, the edge portions of the tooth cannot be cut from the metal material towards the tooth surface, insofar as one of the teeth or one of the left and right sides of the same tooth are concerned. On the other hand, it becomes impossible from time to time to cut the tooth from the tooth towards outside during formation of the tooth cavity, as a result of which a gap tending to produce secondary caries may be produced between the metal prosthetic material and the tooth or a smooth edge portion cannot be produced by cutting.

SUMMARY OF THE INVENTION

In view of the above-described problems of the prior art, it is an object of the present invention to provide a dental handpiece in which the direction of rotation of the dental tool may be selected freely to optimize the grinding direction to thus prevent a gap tending to produce secondary caries from being formed between the metal prosthetic material and the tooth and to enable a smooth marginal edge to be produced.

The above and other objects of the present invention will become apparent from the following description.

According to the present invention, there is provided a dental handpiece having a turbine rotatable in reverse comprising a main handpiece body, a turbine head mounted at a distal end of the main handpiece body, a plurality of turbine vanes for rotatably driving a dental tool removably mounted within the turbine head, a first air supply passage for ejecting compressed air to one surface of each of the turbine vanes for rotating the turbine vanes in one direction, a second air supply passage for ejecting compressed air to the other surface of each of the turbine vanes for rotating the turbine vanes in the other direction, and an air discharge passage for discharging the compressed air.

PREFERRED EMBODIMENTS OF THE INVENTION

Figure 1:
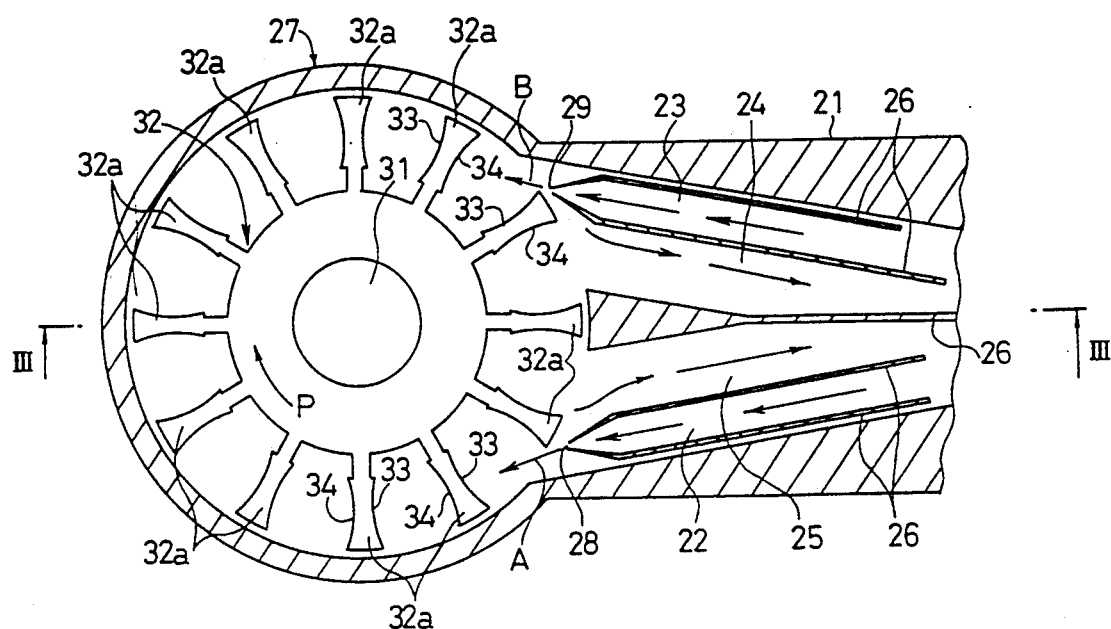
FIG. 1 is a cross-sectional plan view showing a distal part of a dental handpiece according to an embodiment of the present invention.
Figure 2:
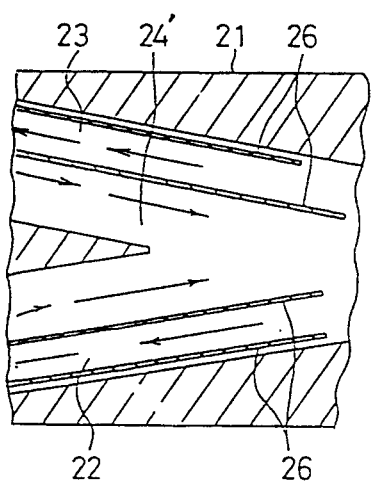
FIG. 2 is a cross-sectional plan view showing an air discharge passage of other type than that shown in FIG. 1.

Referring to FIG. 1, an air supply passage 22 for forward rotation, an air supply passage 23 for reverse rotation, an air discharge passage 24 for forward rotation and an air discharge passage 25 for reverse rotation are defined in isolation from one another within the inside of a handle part 21 of a dental handpiece. The passages 22 to 25 are isolated from one another by partitions 26. Each of the passages 22 to 25 has one end facing the inside of a turbine head 27. At the other end, each of the air supply passages 22, 23 is connected to each of air transport pipes, not shown, adapted for selectively supplying air to one of the air supply passages 22, 23, while each of the air discharge passages 24, 25 is connected to each of air transport pipes, later described, adapted for selectively discharging air from one of these discharge passages 24, 25. Each of the opening ends of compressed air blow-out openings 28, 29 of the air supply passages 22, 23 has a diameter sufficiently smaller than the passages 22, 23. In the embodiment illustrated, the air supply passages 22, 23 are arranged in radially outer regions within the handle part 21 of the handpiece with the blow-out openings 28, 29 being oriented for blowing out compressed air in the directions shown by arrows A and B. Meanwhile, the air discharge passages 24, 25 need not necessarily defined by the partition 26 and may be unified into one passage 24' by removing the central partition 26, as shown in FIG. 2.

The turbine head 27 has a substantially columnar inside space within which a turbine blade 32 rotated in unison with the center shaft 31 is mounted. Each vane 32a of the turbine blade 32 has concave-shaped front and rear pressure-receiving surfaces 33, 34, with the air pressure emanating from the blow-out opening 28 in the direction shown by arrow A acting on the pressure-receiving surface 33 and with the air pressure emanating from the blow-out opening 29 in the direction shown by arrow B acting on the pressure-receiving surface 34.

Figure 3:
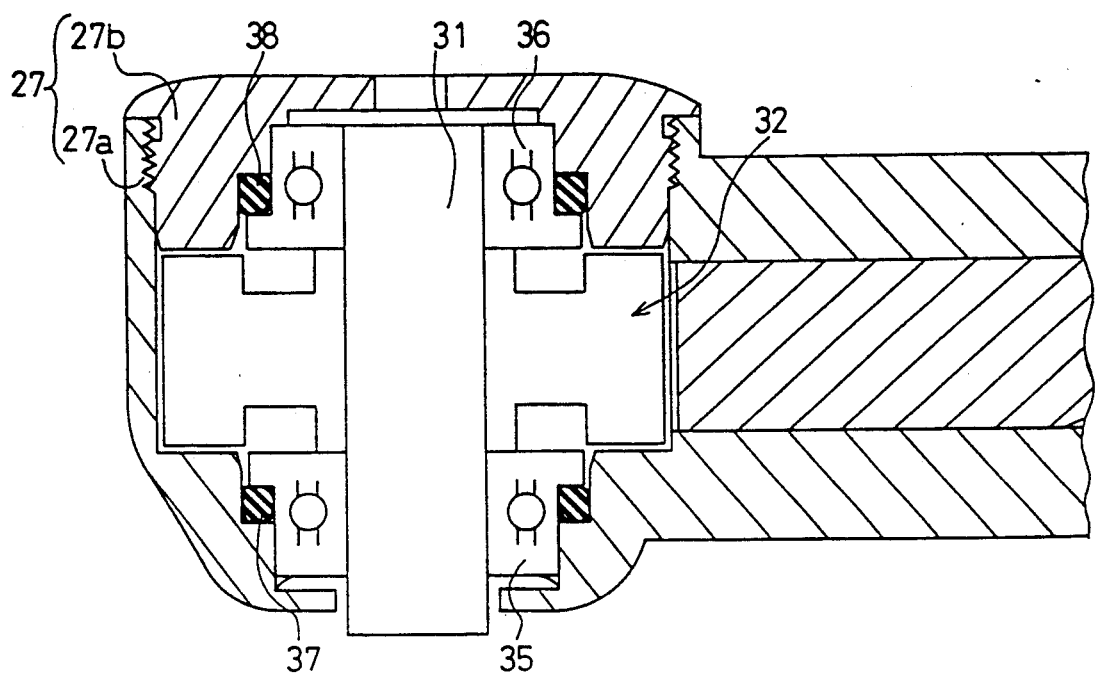
FIG. 3 is a cross-sectional view taken along line III—III of FIG. 1.

The turbine head 27 has a turbine casing 27a and a head cap 27b threadedly attached to and closing the turbine casing 27a, as shown in FIG. 3. The turbine blade 32 is mounted on the center shaft 31 which is supported for rotation by a pair of bearings 35, 36. It is noted that the bearings 35, 36 are secured to the turbine head 27a and to the head cap 27b, respectively, with rubber rings 37, 38 interposed in-between, respectively.

Figure 4:
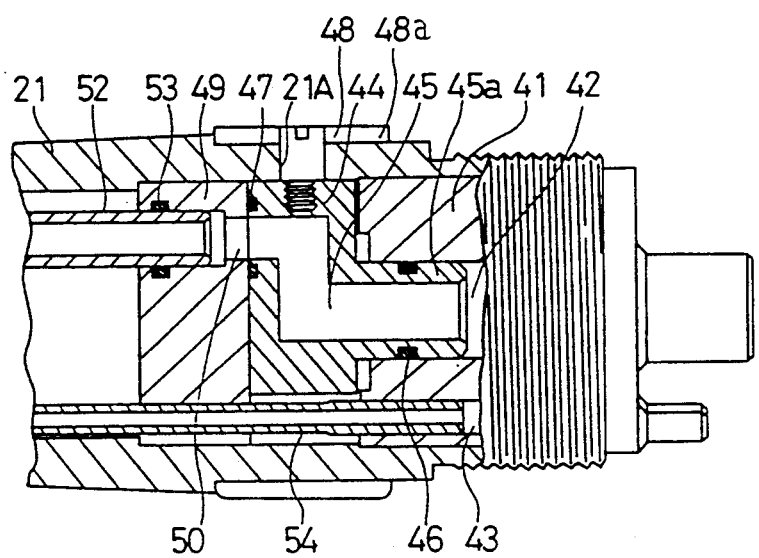
FIG. 4 is a cross-sectional view showing the construction of a rear end of the handle part of the dental handpiece shown in FIG. 1.
Figure 5:
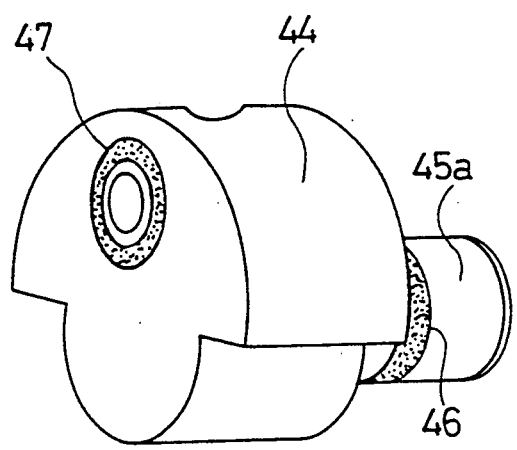
FIG. 5 is a perspective view showing an air cock built into the rear end of the handle part of the dental handpiece shown in FIGS. 1 and 3.
Figure 6:
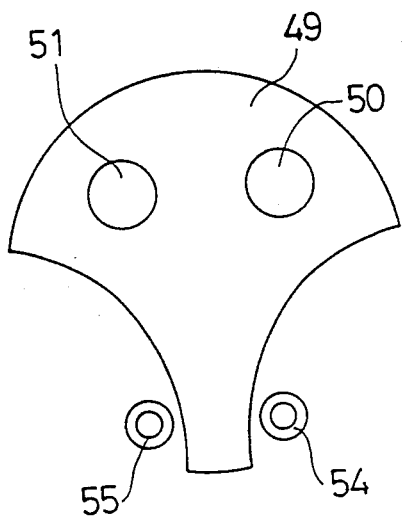
FIG. 6 is a left-hand side view showing an intermediate joint built into the rear end of the handle part of the handpiece shown in FIGS. 1 and 3.
Figure 7:
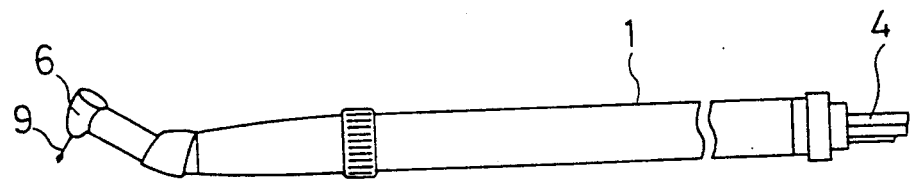
FIG. 7 is a perspective view showing a conventional dental handpiece in its entirety.
Figure 8:
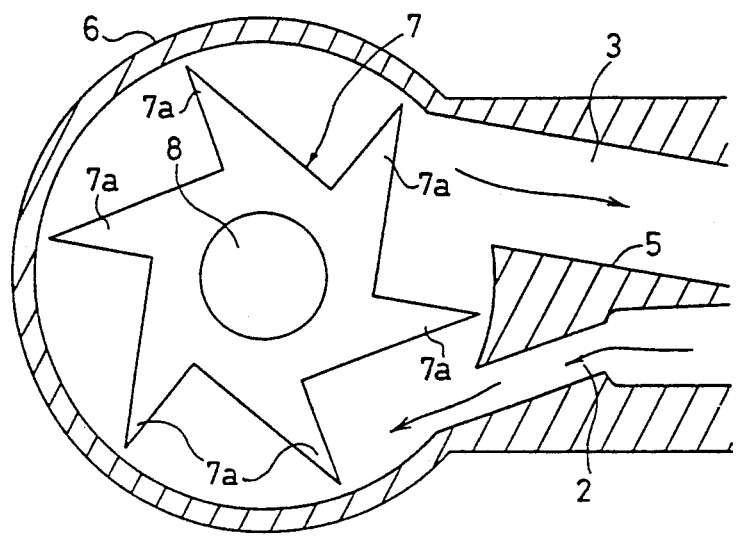
FIG. 8 is a cross-sectional plan view showing a distal part of the conventional dental handpiece shown in FIG. 7.
Figure 9:
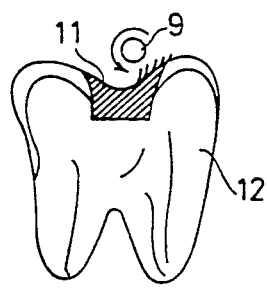
FIG. 9 is a perspective view showing the state of cutting the edge portion of a metal prosthetic material.
Figure 10:
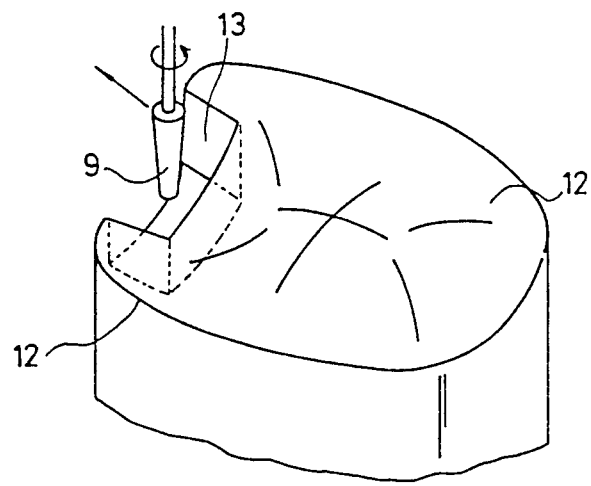
FIG. 10 is a perspective view showing the state of forming a cavity in the tooth.

Referring to FIG. 4 showing the rear portion of the handpiece handle part 21, a block 41 has a main air conduit 42 for compressed air and a main air discharge conduit, not shown, with an end of the main air conduit 42 partially extending out of the handle part 21 for connection to an air tube 4 as shown in FIG. 7. A water supply conduit 43 is also provided in the block 41 in parallel with a chip air passage, not shown, and has its end similarly extending out of the handle part 21. An air cock 44 is constituted by an air supply conduit 45 having its projecting portion 45a fitted within the main air conduit 42 via a sealing ring 46 and is slidably and rotatably fitted about the projecting portion 45a as shown in FIG. 4. At the projecting portion 45a, the air supply conduit 45 is mounted coaxially with the main air conduit 42. The air supply conduit 45 has its left-hand opening end offset from the main air conduit 42 and a sealing ring 47 is provided at the opening end. An operating ring 47 is threadedly attached to the outer peripheral knob 48 of the air cock 44 so as to be moved along a circumferential guide recess 21A formed along the peripheral wall of the handle part 21. Meanwhile, the operating knob 48 may be locked at a desired circumferential position by threading the knob 48 until its flange 48a is pressed against the outer periphery of the handle part 21. An intermediate joint 49 is secured within the handle part 21 and is provided with two guide passages 50, 51, as shown in FIG. 6, in which there are guided two air transport pipes, only one 52 of which is shown in FIG. 4, so that compressed air may be introduced into one of the air supply passages 22, 23 shown in FIG. 1. It is noted that the right-hand end face of the intermediate joint 49 is contacted with a left-hand end face of the air cock 44 via a sealing ring 47. A sealing ring 53 is provided in the intermediate joint 49 for sealing the pipe 52. A piping 54 and another piping, not shown, provided in parallel to the piping 54, are connected to the water supply conduit 43 and to a chip air passage, not shown of the same shape as the water supply conduit 43. These pipings are passed through the intermediate joint 49 for supplying rinse water and chip air into the turbine head 27 via a water supply passage and a chip air conduit, not shown. The air cock 44 is actuated by rotation of the operating knob 48 for selectively connecting the air supply conduit 45 of the air cock 44 with one of the two guide passages 50, 51 within the intermediate joint 49 (see also FIG. 6).

In operation, if the dental tool 9 is to be rotated in a forward direction for cutting, e.g. the metal prosthetic material 11 buried in the tooth in the oral cavity, the operating knob 48 provided in the handle part 21 is actuated for rotating the air cock 44 for connecting one end of the air supply conduit 45 to the guide conduit 50. In this manner, conduit selection is performed so that compressed air supplied via the air tube 4 is conducted via the main air conduit 42, the air supply conduit 45, the guide passage 50 and the pipe 52 to the first air supply passage 22. This causes air discharged via the blow-out opening 28 to impinge on the pressure-receiving surface 33 of each vane 32a of the turbine blade 32 for rotating the turbine blade 32 in a positive direction shown by arrow P in FIG. 1 and also rotating the dental tool 9 in the same direction for carrying out dental treatment. At this time, air confined between the vanes 32a is discharged by the rotation of the turbine blade 32 out of the handle part 1 via the first air discharge passage 24.

When the dental tool 9 is rotated in a reverse direction, the operating knob 48 is actuated for rotating the air cock 44 in the reverse direction for connecting one end of the air supply conduit 45 to the guide passage 51. In this manner, conduit selection is performed so that compressed air supplied via the air tube 4 is conducted via the main air conduit 42, the air supply conduit 45, the guide passage 51 and a pipe, not shown, mounted in parallel to the pipe 52, to the second air supply passage 23. This causes air discharged via the blow-out opening 29 to impinge on the pressure-receiving surface 34 of each vane 32a of the turbine blade 32 for rotating the turbine blade 32 in a direction opposite to that shown by arrow P in FIG. 1 and also rotating the dental tool 9 in the same reverse direction for carrying out dental treatment. At this time, air confined between the vanes 32a is discharged by the rotation of the turbine blade 32 out of the handle part 21 via the second air discharge passage 25.

Since the dental tool 9 may be rotated in forward and reverse directions in a desired manner, the edges of the metal prosthetic material loaded on the tooth within the narrow oral cavity may be perpetually cut from the metal side towards the tooth surface. In addition, when cutting the edges of a side chamber for forming the cavity, the dental tool 9 may be rotated in a direction proceeding from the tooth towards an outside air space to improve the cutting accuracy to prevent secondary caries from being produced.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece having a turbine rotatable in reverse, comprising:
    a main handpiece body,
    a turbine head mounted at a distal end of the main handpiece body,
    a plurality of turbine vanes for rotatably driving a dental tool removably mounted within said turbine head,
    a first air supply passage for ejecting compressed air to one surface of each of said turbine vanes for rotating said turbine vanes in one direction, said first air supply passage having a first nozzle-shaped distal end,
    a second air supply passage for ejecting compressed air to the other surface of each of said turbine vanes for rotating said turbine vanes in the other direction, said second air supply passage having a second nozzle-shaped distal end, and
    an air discharge passage for discharging said compressed air, said air discharge passage having a larger cross-sectional area than those of said respective first and second nozzle-shaped distal ends of both said first and second air supply passages.

2. The dental handpiece according to claim 1 wherein said air discharge passage comprises a first air discharge passage for discharging compressed air during rotation of said turbine vanes in said one direction and a second air discharge passage for discharging compressed air during rotation of said turbine vanes in said other direction.

3. The dental handpiece according to claim 1 wherein said air discharge passage comprises a single air discharge passage for discharging compressed air during rotation of said turbine vanes in said one direction and in said other direction.

4. The dental handpiece according to claim 1 wherein each of the turbine vanes has a concave-shaped pressure-receiving surface on its both sides for receiving said compressed air.

5. The dental handpiece according to claim 1 further comprising switching means for supplying said compressed air to one of a first compressed air transporting pipe communicating with said first air supply passage and a second compressed air transporting pipe communicating with said second air supply passage.

6. The dental handpiece according to claim 5 wherein said switching means comprises a central connecting conduit portion extending along a longitudinal axis of said main handpiece body and connected to a compressed air supply pipe communicating with a compressed air source, an offset conduit portion extending radially outwardly from said central connecting conduit portion and then extending parallel to the longitudinal axis of said main handpiece body, and an operating knob provided on an outer surface of said main handpiece body and operatively associated with said offset conduit portion, said operating knob being operated for supplying compressed air to one of said first compressed air transporting pipe and said second compressed air transporting pipe.

7. The dental handpiece according to claim 6 wherein said offset conduit portion communicates with one of said first and second compressed air transporting pipes via a stationary member adapted for receiving and fixing said first and second compressed air transporting pipes.

* * * * *